(12) United States Patent
Parins

(10) Patent No.: US 8,409,114 B2
(45) Date of Patent: Apr. 2, 2013

(54) COMPOSITE ELONGATE MEDICAL DEVICE INCLUDING DISTAL TUBULAR MEMBER

(75) Inventor: David J. Parins, Corcoran, MN (US)

(73) Assignee: Boston Scientific Scimed, Inc., Maple Grove, MI (US)

( * ) Notice: Subject to any disclaimer, the term of this patent is extended or adjusted under 35 U.S.C. 154(b) by 909 days.

(21) Appl. No.: 11/833,117

(22) Filed: Aug. 2, 2007

(65) Prior Publication Data

US 2009/0036833 A1 Feb. 5, 2009

(51) Int. Cl.
*A61M 25/09* (2006.01)
*A61M 25/00* (2006.01)

(52) U.S. Cl. .................. 600/585; 604/525; 604/164.13

(58) Field of Classification Search .................. 600/585; 604/525, 164.13
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |

(Continued)

FOREIGN PATENT DOCUMENTS

| | | |
|---|---|---|
| AU | 723040 | 12/1997 |
| AU | 733966 | 4/1998 |

(Continued)

OTHER PUBLICATIONS

"Mechanical Design and Systems Handbook", H.A. Rothbart, 1964, p. 33-13 (one sheet).

*Primary Examiner* — Sean Dougherty

(74) *Attorney, Agent, or Firm* — Seager, Tufte & Wickhem, LLC

(57) ABSTRACT

An intracorporeal device includes a shaft having a proximal section including a first elongate member and a distal section including a tubular member and a second elongate member. A proximal region of the tubular member is attached to the distal region of the first elongate member. The second elongate member is disposed within the lumen of the tubular member, and a proximal region of the second elongate member is attached to the proximal region of the elongate tubular member. As such, in some embodiments, the tubular member can function both as a member joining the first and second elongate members, and as a structural element in the distal section of the shaft providing for desired flexibility, torqueability, and/or pushability characteristics.

38 Claims, 4 Drawing Sheets

U.S. PATENT DOCUMENTS

| | | |
|---|---|---|
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |

| Patent | Date | Name |
|---|---|---|
| 5,682,894 A | 11/1997 | Orr et al. |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,971,975 A | 10/1999 | Mills et al. |
| 5,980,471 A | 11/1999 | Jafari |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| RE37,148 E | 4/2001 | Shank |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,296,616 B1 | 10/2001 | McMahon |
| 6,296,631 B1 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,579,246 B2 | 6/2003 | Jacobsen et al. |
| 6,602,207 B1 | 8/2003 | Mam et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,682,493 B2 | 1/2004 | Mirigian |
| 6,689,120 B1 | 2/2004 | Gerdts |
| 6,702,762 B2 | 3/2004 | Jafari et al. |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |
| 7,074,197 B2 | 7/2006 | Reynolds et al. |
| 7,153,277 B2 | 12/2006 | Skujins et al. |
| 7,182,735 B2 | 2/2007 | Shireman et al. |
| 2002/0013540 A1 | 1/2002 | Jacobsen et al. |
| 2002/0019599 A1 | 2/2002 | Rooney et al. |
| 2002/0156397 A1 | 10/2002 | Cornish et al. |
| 2003/0009208 A1 | 1/2003 | Snyder et al. |
| 2003/0060732 A1 | 3/2003 | Jacobsen et al. |
| 2003/0069522 A1 | 4/2003 | Jacobsen et al. |
| 2003/0216668 A1 | 11/2003 | Howland et al. |
| 2004/0087876 A1 | 5/2004 | Eskuri |
| 2004/0116831 A1 | 6/2004 | Vrba |
| 2004/0142643 A1 | 7/2004 | Miller et al. |
| 2004/0167436 A1 | 8/2004 | Reynolds et al. |
| 2004/0167437 A1 | 8/2004 | Sharrow et al. |
| 2004/0167441 A1 | 8/2004 | Reynolds et al. |
| 2004/0181174 A2 | 9/2004 | Davis et al. |
| 2004/0181176 A1 | 9/2004 | Jafari et al. |
| 2006/0121218 A1 | 6/2006 | Obara et al. |
| 2006/0122537 A1 | 6/2006 | Reynolds et al. |
| 2006/0189896 A1 | 8/2006 | Davis et al. |
| 2006/0264904 A1 | 11/2006 | Kerby et al. |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |

| | | | |
|---|---|---|---|
| 2008/0021401 A1 | 1/2008 | Jacobsen et al. | |
| 2008/0021402 A1 | 1/2008 | Jacobsen et al. | |
| 2008/0021403 A1 | 1/2008 | Jacobsen et al. | |
| 2008/0021404 A1 | 1/2008 | Jacobsen et al. | |
| 2008/0021405 A1 | 1/2008 | Jacobsen et al. | |
| 2008/0021406 A1 | 1/2008 | Jacobsen et al. | |
| 2008/0021407 A1 | 1/2008 | Jacobsen et al. | |
| 2008/0021408 A1 | 1/2008 | Jacobsen et al. | |
| 2008/0077119 A1 | 3/2008 | Snyder et al. | |

FOREIGN PATENT DOCUMENTS

| | | |
|---|---|---|
| BR | PI 9712829 | 1/2000 |
| CA | 2266685 | 5/2006 |
| CA | 2255781 | 3/2007 |
| CN | 1230914 | 10/1999 |
| DE | 2539191 | 3/1976 |
| DE | 285514 | 12/1990 |
| EP | 0 045 931 | 2/1982 |
| EP | 0 069 522 | 1/1983 |
| EP | 0 087 933 | 9/1983 |
| EP | 0 111 044 | 6/1984 |
| EP | 0 181 174 | 5/1986 |
| EP | 0 377 453 | 7/1990 |
| EP | 0 565 065 | 6/1996 |
| EP | 0 778 038 | 6/1997 |
| EP | 0 778 039 | 6/1997 |
| EP | 0 778 040 | 6/1997 |
| EP | 0 812 599 | 12/1997 |
| EP | 0 865 772 | 9/1998 |
| EP | 0 865 773 | 9/1998 |
| EP | 0 521 595 | 5/1999 |
| EP | 0 917 885 | 5/1999 |
| EP | 0 937 481 | 8/1999 |
| EP | 0 790 066 | 4/2000 |
| EP | 0 608 853 | 4/2003 |
| EP | 0 935 947 | 12/2004 |
| EP | 0 934 141 | 11/2005 |
| GB | 2214354 | 8/1989 |
| GB | 2257269 | 1/1993 |
| JP | 58-8522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-309159 | 11/1993 |
| JP | 5-507857 | 11/1993 |
| JP | 6-501179 | 2/1994 |
| JP | 631749 | 4/1994 |
| JP | 6169996 | 6/1994 |
| JP | 6-63224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8-229888 | 9/1996 |
| JP | 8509141 | 10/1996 |
| JP | 8317988 | 12/1996 |
| JP | 9000164 | 4/1997 |
| JP | 9-276413 | 10/1997 |
| JP | 9276413 | 10/1997 |
| JP | 9-294813 A | 11/1997 |
| JP | 9294813 | 11/1997 |
| JP | 10-118193 | 5/1998 |
| JP | 10328191 | 12/1998 |
| JP | 11-267224 A | 10/1999 |
| JP | 2000-197704 A | 7/2000 |
| JP | 2000-510722 A | 8/2000 |
| JP | 2000-511083 A | 8/2000 |
| JP | 2001-500808 A | 1/2001 |
| JP | 2002-529137 A | 9/2002 |
| JP | 2002-542901 A | 12/2002 |
| JP | 2002-543896 A | 12/2002 |
| JP | 2003-517893 A | 6/2003 |
| JP | 3649604 | 2/2005 |
| JP | 2005-534407 | 11/2005 |
| JP | 3325828 | 7/2007 |
| SU | 712908 | 1/1980 |
| SU | 758421 | 8/1980 |
| SU | 1529365 | 12/1989 |
| WO | WO 90/02520 | 3/1990 |
| WO | WO 91/13364 | 9/1991 |
| WO | WO 92/04072 | 3/1992 |
| WO | WO 92/07619 | 5/1992 |
| WO | WO 93/04722 | 3/1993 |
| WO | WO 93/11313 | 6/1993 |
| WO | WO 95/24236 | 9/1995 |
| WO | WO 96/19255 | 6/1996 |
| WO | WO 97/10022 | 3/1997 |
| WO | WO 97/25914 | 7/1997 |
| WO | WO 97/43949 | 11/1997 |
| WO | WO 97/44083 | 11/1997 |
| WO | WO 97/44086 | 11/1997 |
| WO | WO 98/10694 | 3/1998 |
| WO | WO 99/04847 | 2/1999 |
| WO | WO 99/11313 | 3/1999 |
| WO | WO 00/27303 | 5/2000 |
| WO | WO 00/30710 | 6/2000 |
| WO | WO 00/48645 | 8/2000 |
| WO | WO 00/57943 | 10/2000 |
| WO | WO 00/66199 | 11/2000 |
| WO | WO 00/67845 | 11/2000 |
| WO | WO 00/72907 | 12/2000 |
| WO | WO 01/28620 | 4/2001 |
| WO | WO 01/36034 | 5/2001 |
| WO | 0145912 | 6/2001 |
| WO | WO 01/45773 | 6/2001 |
| WO | WO 01/93920 | 12/2001 |
| WO | WO 02/13682 | 2/2002 |
| WO | WO 02/062540 | 8/2002 |
| WO | WO 03/004086 | 1/2003 |
| WO | WO 03/008148 | 1/2003 |
| WO | WO 2004/012804 | 2/2004 |
| WO | 2004047899 | 6/2004 |

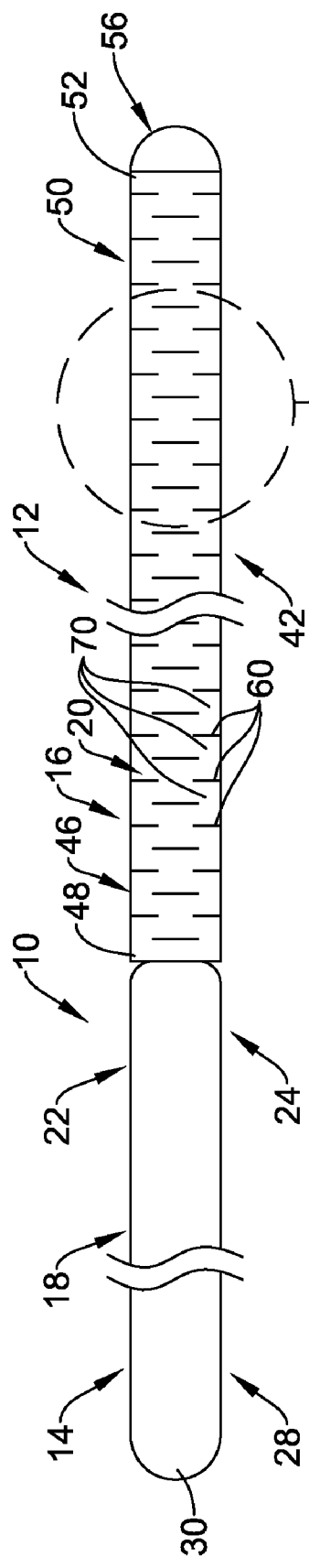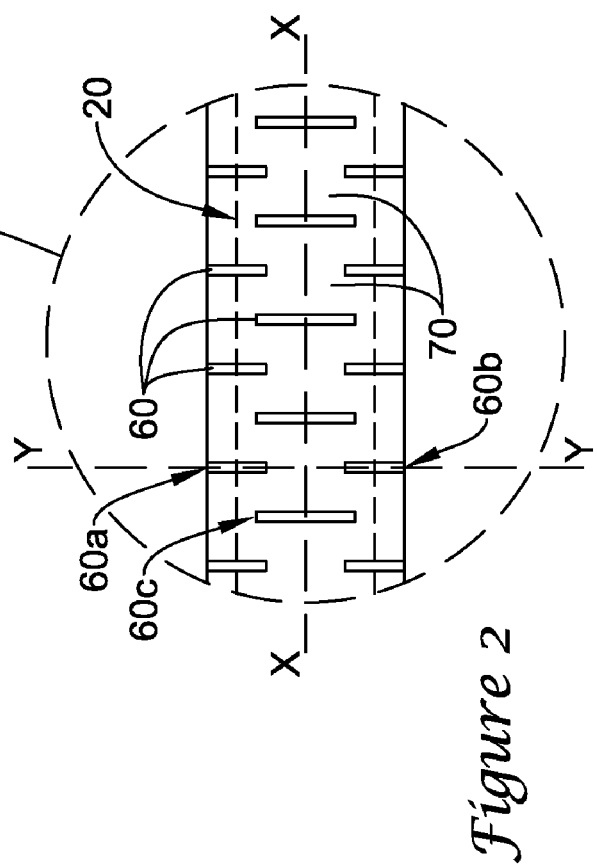
Figure 1
Figure 2

COMPOSITE ELONGATE MEDICAL DEVICE INCLUDING DISTAL TUBULAR MEMBER

TECHNICAL FIELD

The invention pertains generally to elongate medical devices such as catheters, guidewires, and the like.

BACKGROUND

A wide variety of medical devices such as catheters and guidewires have been developed. Medical devices such as catheters and guidewires can be used for performing intravascular procedures. These intravascular procedures have become commonly used in order to avoid more invasive surgical procedures. Because the anatomy of a patient may be very tortuous, it can be desirable to have particular performance features in an elongate medical device. A number of different structures and assemblies for elongate medical devices such as catheters and guidewires are known, each having certain advantages and disadvantages. However, there is an ongoing need to provide alternative structures and assemblies.

SUMMARY OF SOME EMBODIMENTS

The invention provides several alternative designs, materials and methods of manufacturing alternative medical device structures and assemblies.

Accordingly, an example embodiment can be found in an intracorporeal medical device including two elongated members interconnected by an elongated metallic tubular member that not only interconnects the two elongated members, but also extends distally over a distal portion of the device. For example, the intracorporeal device may include first and second elongate members, each having a proximal region, a proximal end, a distal region, and a distal end. The device may further include an elongate tubular member comprising a metallic material and defining a lumen there through, the tubular member having a proximal region, a proximal end, a distal region, and a distal end. The proximal region of the tubular member is attached to the distal region of the first elongate member. Additionally, the second elongate member is disposed within the lumen of the tubular member, and the proximal region of the second elongate member is attached to the proximal region of the tubular member. Other embodiments may include additional structures and/or materials, and/or may relate to methods of making or using an intracorporeal medical device.

The above summary of some embodiments is not intended to describe each disclosed embodiment or every implementation of the present invention. The Figures, and Detailed Description which follows, more particularly exemplify these embodiments.

BRIEF DESCRIPTION OF THE FIGURES

The invention may be more completely understood in consideration of the following detailed description of various embodiments of the invention in connection with the accompanying drawings, in which:

FIG. 1 is a side view of one embodiment of an elongate medical device;

FIG. 2 is a magnified side view of a portion of the distal region of the device shown in FIG. 1;

Figure 2A:
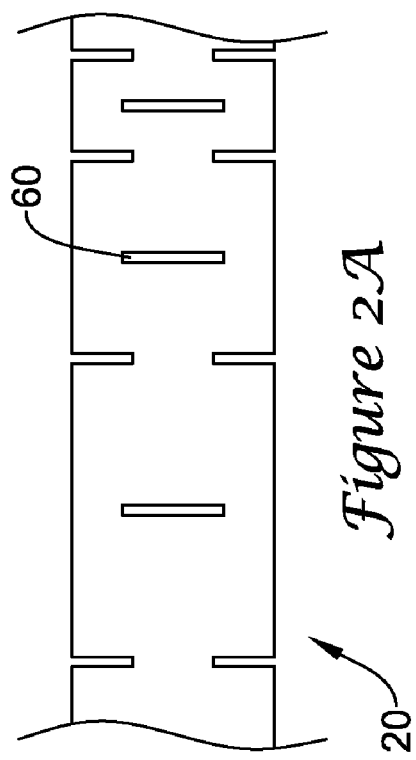
FIG. 2A is a side view of a portion of an alternative distal region of the device shown in FIG. 1.

While the invention is amenable to various modifications and alternative forms, some specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

For example, although discussed with specific reference to guidewires in the particular embodiments described herein, the invention may be applicable to a variety of medical devices that are adapted to be advanced into the anatomy of a patient through an opening or lumen. For example, the invention may be applicable to fixed wire devices, catheters (e.g., balloon, stent delivery, etc.) drive shafts for rotational devices such as atherectomy catheters and IVUS catheters, endoscopic devices, laproscopic devices, embolic protection devices, spinal or cranial navigational devices, and other such devices. Additionally, while some embodiments may be adapted or configured for use within the vasculature of a patient, other embodiments may be adapted and/or configured for use in other anatomies. It is to be understood that a broad variety of materials, dimensions and structures can be used to construct suitable embodiments, depending on the desired characteristics. The following examples of some embodiments are included by way of example only, and are not intended to be limiting.

Refer now to FIG. 1, which is a side view of one example embodiment of an elongate medical device 10, which in this embodiment is shown as a medical guidewire, for example, an intravascular guidewire. The device 10 includes an elongate shaft 12 having a proximal section 14 and a distal section 16. The shaft 12 can include and/or be made up of a plurality of structures, for example a proximal structure and/or assembly 18 extending along the proximal section 14, and a distal structure and/or assembly 20 extending along the distal section 16. As will be discussed in more detail below, the proximal and distal structures and/or assemblies 18/20 are interconnected with each other to form the shaft 12.

Figure 3:
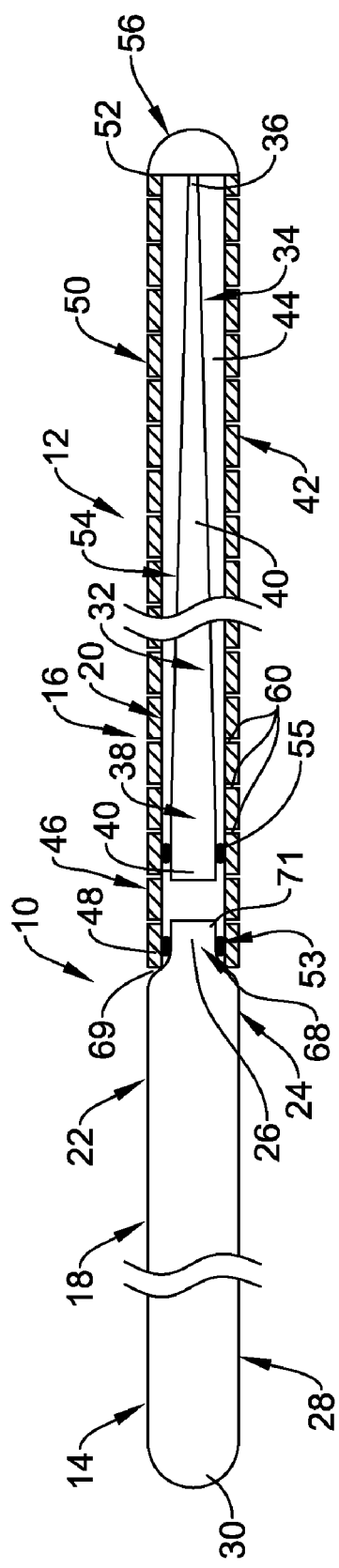
FIG. 3 is a partial cross-sectional view of the device of FIG. 1.

With reference now to FIG. 3, in this embodiment, the proximal structure and/or assembly 18 includes first (e.g., proximal) elongate member 22 having a distal region 24, a distal end 26, a proximal region 28, and a proximal end 30. The distal structure and/or assembly 20 can include a second (e.g., distal) elongate member 32 having a distal region 34, a distal end 36, a proximal region 38, and a proximal end 40. The distal structure and/or assembly 20 can further include an elongate tubular member 42 defining a lumen 44 therethrough, and including a proximal region 46, a proximal end 48, a distal region 50, and a distal end 52.

The proximal and distal structures and/or assemblies 18/20 can be interconnected, for example, as follows. The proximal region 46 of the tubular member 42 can be attached to the distal region 24 of the first (e.g., proximal) elongate member 22, for example, at attachment region and/or point 53. For example, the distal end 26, or a portion thereof or adjacent thereto, of the first elongate member 22 can be attached to the proximal end 48, or a portion thereof or adjacent thereto, of the elongate tubular member 42. Additionally, the second, or distal, elongate member 32 can be disposed within the lumen 44 of the tubular member 42, and the proximal region 38 of the second elongate member 32 can be attached to the proximal region 46 of the elongate tubular member 42, for example, at attachment region and/or point 55. For example, the proximal end 40, or a portion thereof or adjacent thereto, of the second elongate member 32 can be attached to the proximal end 48, or a portion thereof or adjacent thereto, of the elongate tubular member 42. The attachments between the tubular member 42 and the first elongate member 22 and between the tubular member 42 and the second elongate member 32 can be achieved using any of a broad variety of attachment techniques and/or structures, some examples of which will be discussed in more detail below with reference to FIGS. 3-7.

As can be appreciated, the first and second elongate members 22/32 are both attached to the elongated tubular member 42 which links the two elongated members 22/32 together. The linking can be achieved such that the first and second elongate members 22/32 and the elongated tubular member 42 extend generally along a common longitudinal axis. In some embodiments, as shown, the first elongate member 22 and the second elongate member 32 are not directly attached, or even in direct contact with one another, but rather are linked together via the elongated tubular member 42. As such, in some embodiments, the tubular member 42 can function both as a member joining the first and second elongate members 22/32 and as a structural element in the distal section 16 of the shaft 12—providing for desired flexibility, torqueability, and/or pushability characteristics as will be discussed in more detail below.

The tubular member 42 can extend distally such that at least a portion of the distal region 50 of the tubular member 42 is disposed adjacent to or distally of the distal region 34 of the second elongate member 32. For example, in some embodiments, the distal end 52 of the tubular member 42 can be disposed adjacent to or distally of the distal end 36 of the second elongate member 32. However, it should be understood that this is not necessary in all embodiments, and in some other embodiments, the distal end 36 of the second elongate member 32 may extend distally of the distal end 52 of the tubular member 42, but at least a portion of the distal region 50 of the tubular member 42 may still be disposed adjacent to at least a portion of the distal region 34 of the second elongate member 32. As such, the elongated tubular member 42 can function as a structural element in the distal section 16 of the shaft 12 and/or the device 10—as well as a linking structure between the elongate members 22/32.

The second elongate member 32 can extend within the lumen 44 of the tubular member 42 along a substantial portion of the length of the tubular member 42. For example, in the embodiment shown, the second elongate member 32 extends distally from its proximal end 40, which is within the proximal region 46 and can be near or adjacent the proximal end 48 of the tubular member 42, to its distal end 36, which is within the distal region 50 and can be adjacent the proximal end 52 of the tubular member 42. While in other embodiments, it is not necessary for the second elongate member 32 to extend this far along the length of the tubular member 42, in at least some embodiments, the second elongate member 32 can extend at least about 25%, or at least about 50%, or at least about 75% or more, or may extend along substantially the entire length of the tubular member 42. However, in other embodiments, the second elongate member 32 does not extend along the entire length of the tubular member 42, and ends prior to the proximal or distal ends 48/52 of the tubular member 42, or both.

Additionally, the tubular member 42 and the second elongate member 32 may be sized and/or shaped or otherwise adapted and/or configured such that a space or gap 54 can be defined between at least a portion of the outer surface of the second elongate member 32 and the inner surface of the tubular member 42. For example, the tubular member 42 can include an inner diameter that is greater than the outer diameter of the second elongated member 32 that is disposed therein. As such, the tubular member 42 can be disposed about the second elongated member 32, or a portion thereof, such that the space or gap 54 is defined therebetween. In some embodiments, the gap or space 54 remains open or unfilled by any other structure of the device 10 along substantially the entire length of the second elongated member 32, with the exception of the small attachment point 55. For example, in some embodiments, the gap or space 54 can extend between the outer surface of the second elongated member 32 and the inner surface of the tubular member 42 along the length of the elongated member 32 in the range of about 50% or greater, about 75% or greater, about 90% or greater, or about 95% or greater of the entire length of the elongated member 32. However, in other embodiments, other attachment points between the elongated member 32 and the tubular member 42 may be used, and as a result, multiple gaps or spaces may be created that may be separated by these additional attachment points, which may, in effect, fill portions of the gap 54. Such multiple gaps or spaces may still collectively extend along a substantial portion of the length of the elongated member 32, for example, in percentages of the total length as given above. As such, the tubular member can act to reinforce or impart desired properties, such as tortional or pushable rigidity, to the shaft 12, but allow at least the portion of the elongated member 32 surrounded by the gap or space 54 to move laterally within the lumen 44. In yet other embodiments, one or more other structures, such as one or more coils, ribbons, bands, marker members or the like, may be disposed within and fill portions of the gap 54.

The device 10 may also include a distal tip 56 disposed at the distal end thereof. The distal tip 56 may include any of a broad variety of tip structures and/or assemblies, and may be adapted and/or configured to provide certain characteristics, such as atraumatic or flexibility characteristics, to the distal end of the device 10. The distal tip 56 can be formed from a variety of different materials, depending on desired performance characteristics. In some embodiments, the distal tip 56 can include a generally or partially rounded structure to provide an atraumatic element on the distal end of the shaft 12. In some embodiments, the distal tip 56 can be formed of a material such as a metallic material that is amenable to being welded, soldered, or otherwise attached to the distal end of the shaft 12. For example, in some embodiments, the distal tip 56 can be a solder tip or solder ball that is disposed via soldering at the distal end of the device 10 and forms an atraumatic rounded portion. In other embodiments, the distal tip 56 can be a prefabricated, or partially prefabricated structure that is thereafter attached to the distal end of the device using suitable attachment techniques, such as welding, soldering, brazing, crimping, friction fitting, adhesive bonding, mechanical interlocking and the like. A variety of different processes, such as soldering, deep drawing, roll forming or metal stamping, metal injection molding, casting and the like can be used to form such distal tip structures.

In the embodiment shown in FIGS. 1 and 3, the distal tip 56 includes a rounded structure, such as a metallic or solder tip that is attached, for example, to the distal end 52 of the tubular member 42, and/or the distal end 36 of the second elongated member 32, or both (as shown) and/or to other structures near or at the distal end of the device 10. As such, in the embodiment shown, both the tubular member 42 and the second elongated member 32 extend to and/or into the distal tip 56, but as discussed above, this is not necessary in all embodiments. Additionally, other components, such as a ribbon, coil, marker band, centering ring, or the like may also be part of or be disposed adjacent the tip or other portions of the device 10, some examples of which are discussed below with regard to FIG. 8.

Those of skill in the art and others will recognize that the materials, structures, and dimensions of the first and second elongate members 22/32 and the elongated tubular member 42 are dictated primarily by the desired characteristics and function of the final guidewire, and that any of a broad range of materials, structures, and dimensions can be used.

For example, the first and second elongate members 22/32 and the elongated tubular member 42 may be formed of any materials suitable for use, dependent upon the desired properties of the device 10. Some examples of suitable materials include metals, metal alloys, polymers, composites, or the like, or combinations or mixtures thereof. Some examples of suitable metals and metal alloys include stainless steel, such as 304V, 304L, and 316L stainless steel; alloys including nickel-titanium alloy such as linear elastic or superelastic (i.e., pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. In some embodiments, it is desirable to use metals or metal alloys that are suitable for metal joining techniques such as welding; soldering, brazing, crimping, friction fitting, adhesive bonding, etc. The particular material used can also be chosen in part based on the desired flexibility requirements or other desired characteristics.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Within the family of commercially available nitinol alloys is a category designated "linear elastic" which, although is similar in chemistry to conventional shape memory and superelastic (i.e., pseudoelastic) varieties, exhibits distinct and useful mechanical properties. By skilled applications of cold work, directional stress and heat treatment, the wire is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there are no martensite/austenite phase changes detectable by DSC and DMTA analysis in the range of about −60° C. to about 120° C. The mechanical bending properties of such material are, therefore, generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy.

In some embodiments, the linear elastic nickel-titanium alloy is in the range of about 50 to about 60 weight percent nickel, with the remainder being essentially titanium. In some particular embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of suitable nickel-titanium alloys include those disclosed in U.S. Pat. Nos. 5,238,004 and 6,508,803, which are incorporated herein by reference. In some other embodiments, a superelastic alloy, for example a superelastic nitinol, can be used to achieve desired properties.

In some embodiments, the first and second elongate members 22/32 and the elongated tubular member 42, can be made of the same material, or in some embodiments, are made of different materials, or each can include portions or sections thereof that are made of different material. The material used to construct the different portions of the device 10 can be chosen to impart varying characteristics, for example, flexibility and stiffness characteristics, to different portions of the device 10.

For example, in some embodiments, the first (e.g., proximal) elongate member 22 may include or be formed of relatively stiff material such as straightened 304v stainless steel wire. Alternatively, elongate member 22 may include or be formed of a metal or metal alloy such as a nickel-titanium alloy, nickel-chromium alloy, nickel-chromium-iron alloy, cobalt alloy, or other suitable material. In many embodiments, the material used to construct the first (e.g., proximal) elongate member 22 may be selected to be relatively stiff, for example, for pushability and/or torqueability.

In some embodiments, the second (e.g., distal) elongate member 32 may include or be formed of a relatively flexible material such as a super elastic (i.e., pseudoelastic) or linear elastic alloy (e.g., nickel-titanium), or alternatively, a polymer material, such as a high performance polymer. Alternatively, second elongate member 32 may include a metal or metal alloy such as stainless steel, nickel-chromium alloy, nickel-chromium-iron alloy, cobalt alloy, or other suitable material. In many embodiments, the material used to construct the second (e.g., distal) elongate member 32 may be selected to be relatively laterally flexible, for example, for trackability.

In some embodiments, the elongated tubular member 42 may also include or be formed of a relatively flexible material such as a super elastic (i.e., pseudoelastic) or linear elastic alloy (e.g., nickel-titanium), or alternatively, a polymer material, such as a high performance polymer. Alternatively, the elongated tubular member 42 may include a metal or metal alloy such as stainless steel, nickel-chromium alloy, nickel-chromium-iron alloy, cobalt alloy, or other suitable material. In many embodiments, the material used to construct the elongated tubular member 42 may be selected to be relatively laterally flexible for trackability, but may also include structure and or material that also allows for pushability and torqueability, as will be discussed in more detail below.

In some particular embodiments, the first elongate member 22 is formed from a stainless steel wire, the second elongate member 32 is formed from a linear elastic nitinol wire, and the elongate tubular member is formed from a super elastic nitinol tube.

Portions or all of the first or second elongate members 22/32 or the elongated tubular member 42, or other structures included within the device 10, may in some cases be doped with, coated or plated with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like, or combinations or alloys thereof.

Additionally, in some instances a degree of MRI compatibility can be imparted into device 10. For example, to enhance compatibility with Magnetic Resonance Imaging (MRI) machines, the first and/or second elongate members 22/32 and/or the elongated tubular member 42, or other portions of device 10, can be made in a manner that would impart a degree of MRI compatibility. For example, the first and/or second elongate members 22/32 and/or the elongated tubular member 42, or portions thereof, may be made of a material that does not substantially distort the image and create substantial artifacts (artifacts are gaps in the image) during MRI imaging. Certain ferromagnetic materials, for example, may not be suitable because they may create artifacts in an MRI image. The first and/or second elongate members 22/32 and/or the elongated tubular member 42, or portions thereof, may also be made from a material that the MRI machine can image. Some materials that exhibit these characteristics include, for example, tungsten, Elgiloy, MP35N, nitinol, and the like, and others, or combinations or alloys thereof.

The lengths of the first and/or second elongate members 22/32 and/or the elongated tubular member 42 (and/or the length of device 10) are typically dictated by the useful length and flexibility characteristics desired in the final device. For example, proximal section 14 of the shaft 12 may have a length in the range of about 20 to about 300 centimeters or more, the distal section 16 of the shaft 12 may have a length in the range of about 3 to about 50 centimeters or more, and the device 10, such as a guidewire, may have a total length in the range of about 25 to about 350 centimeters or more. It can be appreciated that the lengths of the individual components can be adapted such that the desired length, flexibility, torqueability, and other characteristics are achieved, and that alterations in these lengths can be made without departing from the spirit of the invention.

The first and/or second elongate members 22/32 can have a solid cross-section, for example as solid proximal and distal core wires. However, in some embodiments, the first and/or second elongate members 22/32 can have a hollow cross-section, or yet in other embodiments, can include combinations of areas having solid cross-sections and hollow cross sections. Moreover, first and/or second elongate members 22/32 can include rounded, flattened, oval, rectangular, square, polygonal, and the like, or other such various cross-sectional geometries. Further, the cross-sectional geometries along the length of the first and/or second elongate members 22/32 can be constant or can vary. For example, FIG. 3 depicts first and/or second elongate members 22/32 as having a generally round cross-sectional shape, but it can be appreciated that other cross-sectional shapes or combinations of shapes may be utilized without departing from the spirit of the invention.

Additionally, first and/or second elongate members 22/32 may include one or more tapers or tapered regions. The tapered regions may be linearly tapered, tapered in a curvi-linear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness/flexibility characteristics. It can be appreciated that essentially any portion of device 10 and/or first and/or second elongate members 22/32 may be tapered, and the taper can be in either the proximal or the distal direction. The first and/or second elongate members 22/32 may include one or more portions where the outside diameter is narrowing and portions where the outside diameter remains essentially constant. The number, arrangement, size and length of the narrowing and constant diameter portions can be varied to achieve the desired characteristics, such as flexibility and torque transmission characteristics. For example, in the embodiment shown in FIG. 3, the second elongated member 32 becomes more flexible in the distal region 34 than in the proximal region 38. This variation in flexibility can be achieved, for example, by reducing the cross-sectional area along the length of the second elongated member 32 as it extends distally. The first elongate member 22, however, is shown with a generally uniform cross-sectional area along its length, and as such, may have generally uniform flexibility characteristics along its length. Additionally, either due to its structure (e.g. increased cross-sectional area) or due to flexibility characteristics of the types of materials used, the first elongate member 22 may be less flexible (more stiff) than all or portions of the second elongated member 32. It should be understood, however, that this embodiment is given by way of example, and that in other embodiments, the flexibility characteristics of the first and second elongate members 22/32 may be varied as desired, for example, through the use of alternative structure and/or materials, as discussed above.

In some example embodiments, the outer diameters of the first and second elongate members 22/32 can be in the range of about 0.005 inch to about 0.04 inch. However, it should be appreciated that other sizes may be utilized without departing from the spirit of the invention.

The outer diameter of the first and second elongate members 22/32, including any tapered and/or constant diameter portions, may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing the structure wire during the grinding process. In some embodiments, centerless grinding can be achieved using a Royal Master HI-AC centerless grinder. Some examples of suitable grinding methods are disclosed in U.S. patent application Ser. No. 10/346, 698 filed Jan. 17, 2003 (Pub. No. U.S. 2004/0142643), which is herein incorporated by reference.

Also in some embodiments, portions of the first and/or second elongate members 22/32 may be flattened, for example, to provide for desired flexibility characteristics, or to provide an attachment point for other structure. For example, the second elongate member 32 could include a flattened portion in the distal region 34 thereof adjacent its distal end 36. For example, the distal most about 0.05 inch to about 1 inch of the distal region 34 can be flattened to define generally parallel opposed surfaces, and to have a thickness in the range of about 0.0005 inch to about 0.003 inch.

Additionally, the first and/or second elongate members 22/32 may also include structure that is configured and/or adapted to aid and/or accommodate attachment of the members 22/32 with the tubular member 42. For example, the first and/or second elongate members 22/32 may include tapered and/or reduced diameter portions and/or increased diameter portions near their ends and/or near attachment points that are intended to aid in attachment. Some example embodiments of such structures will be discussed in more detail below, with reference to FIGS. 3-7.

As indicated above, the tubular member 42 generally has a tubular construction having a tubular wall with a hollow cross-section, and defining the lumen 44 extending there through, and the lumen 44 can be adapted and/or configured to house or surround at least a portion of the second elongated member 32. The particular cross-sectional shape of the tubular member 42 can be any desired shape, for example rounded, oval, rectangular, square, polygonal, and the like, or other such various cross-sectional geometries. The cross-sectional geometries along the length of the tubular member 42 can be constant or can vary. For example, FIG. 3 depicts the tubular member 42 as having a generally constant round cross-sectional shape, but it can be appreciated that other cross-sectional shapes or combinations of shapes may be utilized without departing from the spirit of the invention.

Additionally, the tubular member 42 may include one or more tapers or tapered regions, and one or more constant diameter sections, or may generally include a constant inner and outer diameter. The tapers and/or constant diameters may be manifested in variations and/or consistencies in the size of the outer diameter, inner diameter, and/or wall thickness of the tubular member 42. Any tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness/flexibility characteristics. As indicated above with regard to the elongate members 22/32, it can be appreciated that essentially any portion of device 10, and/or the first and/or second elongate members 22/32, and or the tubular member 42 may be tapered or can have a constant diameter, and that any tapers and/or constant diameter can extend in either the proximal or the distal direction, for example, to achieve the desired flexibility/stiffness characteristics. In some embodiments, the tubular member 42 can have an inner diameter, defining the lumen 44, that is in the range of about 0.008 inch to about 0.06 inch in size, and in some embodiments, in the range of about 0.02 inch to about 0.035 inch in size. Additionally, in some embodiments, the tubular member 42 can have an outer diameter that is in the range of about 0.010 inch to about 0.07 in size, and in some embodiments, in the range of about 0.02 inch to about 0.04 inch in size. It should be understood however, that these and other dimensions provided herein are by way of example embodiments only, and that in other embodiments, the size of the inner and outer diameter of the tubular member 42 can vary greatly from the dimensions given, depending upon the desired characteristics and function of the device.

The tubular member 42 can also include structure or otherwise be adapted and/or configured to achieve a desired level of stiffness, torqueability, flexibility, and/or other characteristics. The desired stiffness, torqueability, lateral flexibility, bendability or other such characteristics of the tubular member 42 can be imparted, enhanced, or modified by the particular structure that may be used or incorporated into the tubular member 42. As can thus be appreciated, the flexibility of the tubular member can vary along its length, for example, such that the flexibility can be higher at the distal end relative to the proximal end, or vice versa. However, in some embodiments, the tubular member can have a substantially constant flexibility along the entire length thereof.

One manner of imparting additional flexibility is to selectively remove material from portions of the tubular member 42. For example, with reference to FIGS. 1 and 3, the tubular member 42 may include a thin wall tubular structure including one or a plurality of apertures 60, such as grooves, cuts, slits, slots, or the like, formed in a portion of, or along the entire length of, the tubular member 42. The apertures 60 may be formed such that one or more spines or beams 70 are formed in the tubular member 42. Such spines or beams 70 (FIG. 2) could include portions of the tubular member 42 that remain after the apertures 60 are formed in the body of the tubular member 42, and may act to maintain a relatively high degree of tortional stiffness while maintaining a desired level of lateral flexibility due to the apertures 60. Such structure may be desirable because it may allow tubular member 42, or portions thereof, to have a desired level of laterally flexibility as well as have the ability to transmit torque and pushing forces from the proximal region 46 to the distal region 50. The apertures 60 can be formed in essentially any known way. For example, apertures 60 can be formed by methods such as micro-machining, saw-cutting, laser cutting, grinding, milling, casting, molding, chemically etching or treating, or other known methods, and the like. In some such embodiments, the structure of the reinforcing member 60 is formed by cutting and/or removing portions of the tube to form apertures 60.

In some embodiments, the apertures 60 can completely penetrate the body wall of the tubular member 42 such that there is fluid communication between the lumen 44 and the exterior of the tubular member 42 through the apertures 60. In some embodiments, the apertures 60 may only partially extend into the body wall of the tubular member 42, either on the interior or exterior surface thereof. Some other embodiments may include combinations of both complete and partial apertures 60 through the body wall of the tubular member 42. The shape and size of the apertures 60 can vary, for example, to achieve the desired characteristics. For example, the shape of apertures 60 can vary to include essentially any appropriate shape, such as squared, round, rectangular, pill-shaped, oval, polygonal, elongated, irregular, spiral (which may or may not vary in pitch), or other suitable means or the like, and may include rounded or squared edges, and can be variable in length and width, and the like.

In some embodiments, some adjacent apertures 60 can be formed such that they include portions that overlap with each other about the circumference of the tubular member 42. In other embodiments, some adjacent apertures 60 can be disposed such that they do not necessarily overlap with each other, but are disposed in a pattern that provides the desired degree of lateral flexibility. Additionally, the apertures 60 can be arranged along the length of, or about the circumference of, the tubular member 42 to achieve desired properties. For example, the apertures 60 can be arranged in a symmetrical pattern, such as being disposed essentially equally on opposite sides about the circumference of the tubular member 42, or equally spaced along the length of the tubular member 42, or can be arranged in an increasing or decreasing density pattern, or can be arranged in a non-symmetric or irregular pattern.

Figure 2B:
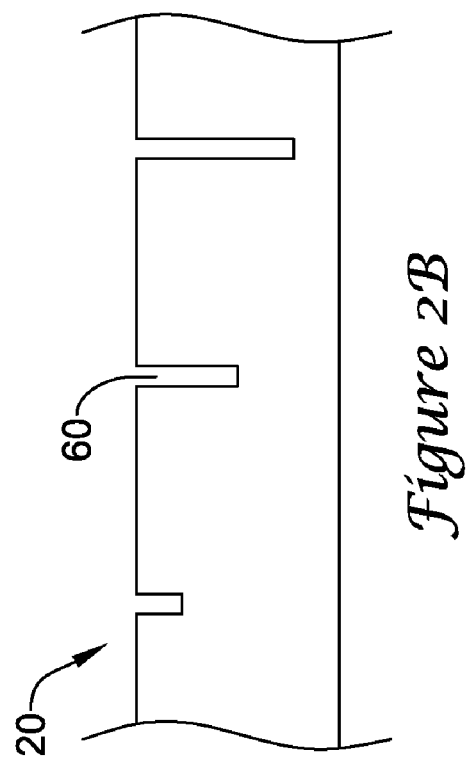
FIG. 2B is a side view of a portion of an alternative distal region of the device shown in FIG. 1.

As can be appreciated, the spacing, arrangement, and/or orientation of the apertures 60, or in the associated spines or beams that may be formed, can be varied to achieve the desired characteristics. For example, the number, proximity (to one another), density (e.g., apertures 60 increasing in density in the distal direction as shown in FIG. 2A), size, shape and/or depth (e.g., apertures 60 increasing in depth in the distal direction as shown in FIG. 2B) of the apertures 60 along the length of the tubular member 42 may vary in either a stepwise fashion or consistently, depending upon the desired characteristics. For example, the number or proximity of apertures 60 to one another near one end of the tubular member 42 may be high, while the number or proximity of apertures 60 to one another near the other end of the tubular member 42, may be relatively low, or vice versa. For example, in the some embodiments, the distal region 50 of the tubular member 42 may include a greater density of apertures 60, while the proximal region 46 of the tubular member 42 may include a lesser density of apertures, or may even be devoid of any apertures 60. As such, the distal region 50 can have a greater degree of lateral flexibility relative to the proximal region 46. It should be understood that similar variations in the size, shape and/or depth of apertures 60 along the length of the tubular member 42 can also be used to achieve desired flexibility differences there along.

In the embodiment shown in FIGS. 1 and 2, the apertures 60 and the associated spines or beams 70 are disposed in a generally uniform pattern along the length of the tubular member 42. In this embodiment, the apertures 60 have a length and a width, and the length of the apertures extend generally perpendicular to the longitudinal axis of the tubular member 42. In other words, the apertures 60 can have a major axis extending along their length that extends radially about the longitudinal axis of the body 42, and the major axis is generally perpendicular to the longitudinal axis of the tubular body 42.

Additionally, in the embodiment shown, the apertures 60 are formed in groups of two, wherein each of the two apertures 60 in the group is disposed at a similar longitudinal point along the length of the tubular member 42, but on opposite side of the tubular member about the circumference thereof. For example, apertures 60a and 60b (FIG. 2) form a pair that is disposed at a longitudinal point along the length of the tubular member, and are formed on opposite sides of the tubular member along the line Y-Y, where the line Y-Y is substantially perpendicular to the axis of the tubular member. Aperture 60c is shown longitudinally spaced from apertures 60a and 60b, and is also substantially perpendicular to the longitudinal axis of the tubular member (its counterpart apertures 60d is not shown because it is on the opposite side of the tubular member). It should be understood, however, that in other embodiments the arrangement of the apertures can be varied to achieve the desired characteristics along the length of the tubular member 42. For example, instead of pairs, only a single aperture, or more than two apertures, may be located at certain points along the length of the device. Additionally, the major axis of the apertures may be disposed at different angles, not necessarily perpendicular to the longitudinal axis of the tubular member 42.

Collectively, these Figures and this Description illustrate that changes in the arrangement, number, and configuration of apertures 60 may vary without departing from the scope of the invention. Some additional examples of arrangements of apertures, such as cuts or slots, formed in a tubular body are disclosed in U.S. Pat. No. 6,428,489, and in U.S. Pat. No. 6,579,246, both of which are incorporated herein by reference. Also, some additional examples of arrangements of cuts or slots formed in a tubular body for use in a medical device are disclosed in a U.S. patent application Ser. No. 10/375,493 filed Feb. 28, 2003 (Pub. No. US 2004/0167437), which is incorporated herein by reference.

The flexibility characteristics of the tubular member 42 could also be achieved using other methods, such as by the addition of material and/or one or more reinforcement members to certain portions of the tubular member 42.

As indicated above, any of a broad variety of attachment techniques and/or structures can be used to achieve the attachments between the tubular member 42 and the first elongate member 22 and between the tubular member 42 and the second elongate member 32, or between any of the structures present in the device 10. Some examples of suitable attachment techniques include welding, soldering, brazing, crimping, friction fitting, adhesive bonding, mechanical interlocking and the like.

Some examples of welding processes that can be suitable in some embodiments include LASER welding, resistance welding, TIG welding, microplasma welding, electron beam welding, friction welding, inertia welding, or the like. LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn.

In some embodiments, LASER or plasma welding can be used to achieve the attachments. In LASER welding, a light beam is used to supply the necessary heat. LASER welding can be beneficial in the processes contemplated by the invention, as the use of a LASER light heat source can provide significant accuracy. It should also be understood that such LASER welding can also be used to attach other components of the device. Additionally, in some embodiments, LASER energy can be used as the heat source for soldering, brazing, or the like for attaching different components or structures of the guidewire together. Again, the use of a LASER as a heat source for such connection techniques can be beneficial, as the use of a LASER light heat source can provide substantial accuracy. One particular example of such a technique includes LASER diode soldering.

Additionally, in some other example embodiments, attachment may be achieved and/or aided through the use of a mechanical connector or body, and/or by an expandable alloy, for example, a bismuth alloy. Some examples of methods, techniques and structures that can be used to interconnect different portions of a guidewire using such expandable material are disclosed in a U.S. patent application Ser. No. 10/375,766 filed Feb. 26, 2003 (Pub. No. U.S. 2004/0167441), which is hereby incorporated herein by reference. Some methods and structures that can be used to interconnect different sections are disclosed in U.S. Pat. No. 6,918,882, and U.S. patent application Ser. No. 10/086,992 filed Feb. 28, 2002 (Pub. No. U.S. 2003/0069521), which are incorporated herein by reference.

Refer now to FIG. 3, which shows one example of an attachment configuration. In this arrangement, the distal end 26 of the first, (e.g., proximal) elongate member 22 has a taper extending into a reduced diameter portion 68, and can form a half hour-glass like shape. The reduced diameter portion 68 includes tapering portion 69 and reduced diameter constant diameter portion 71. This configuration on the distal end 24 may facilitate the accurate placement of the distal end 26 of the first elongate member 22 into the lumen 44 of the elongate member, because the structure of the reduced diameter portion 68 will tend to center the elongate member 22 within the lumen 44. The reduced constant diameter portion 71 extends into the lumen 44, and attachment can be achieved, for example at attachment points/regions 53 along the reduced diameter portion 71 using any of the methods set forth above. Further, the second, (e.g., distal) elongate member 32 can be disposed within the lumen 44 of the tubular member 42, and the proximal region 38 of the second elongate member 32 can be attached to the proximal region 46 of the elongate tubular member 42, for example, at attachment points 55 using any of the methods set forth above. In some other embodiments, additional attachment points between the tubular member 42 and the second elongate member 32 may also be utilized along the length of the second elongate member 32. In some embodiments, the attachments can extend around the entire circumference of the longitudinal axis of the device 10, for example about the entire circumference of the first and second elongate members 22/32. In some other embodiments, however, one or more spaced attachment points/areas can be made around the circumference of the longitudinal axis. The use of certain attachment techniques, for example laser welding or laser diode soldering, or the like, can be useful in making connections around only a portion of the circumference, because they tend to allow the accuracy needed to make such connections. As discussed above, in this embodiment, there is no contact, and no direct bond, between the distal end 26 of the first elongated member 22 and the proximal end 40 of the second elongated member 32. In alternative embodiments, however, there may be contact, or even a bond formed directly between these two elements.

Figure 4:
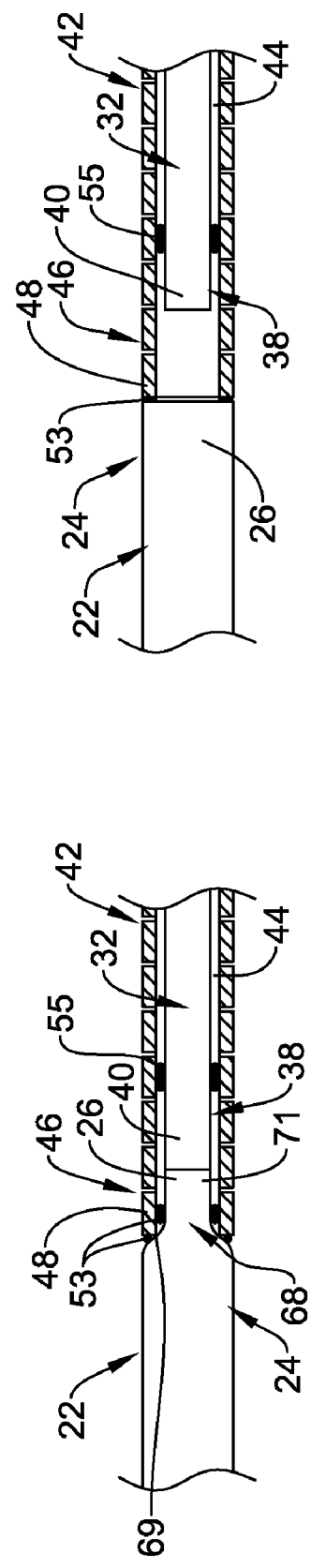
FIG. 4 is a cross-sectional view similar to that of FIG. 3, but showing an alternative construction for the junction between the proximal and distal sections.

For example, refer now to FIG. 4, which shows an embodiment that is in many respects similar to that shown in FIG. 3, with like reference numerals indicate similar structure. In FIG. 4, however, there is contact between the distal end 26 of the first elongated member 22 and the proximal end 40 of the second elongated member 32. These two structures are arranged such that they butt up against each other, but there is no direct bond between the two. In alternative embodiments, however, there may be bond formed directly between these two elements using, for example, any of the attachment techniques discussed above.

Figure 5:
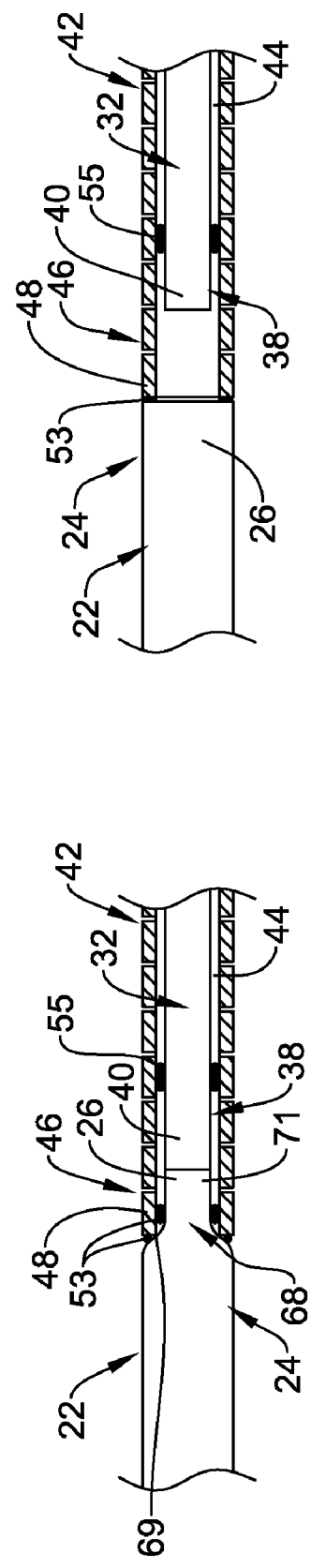
FIG. 5 is a cross-sectional view similar to that of FIG. 3, but showing an alternative construction for the junction between the proximal and distal sections.

Refer now to FIG. 5, which shows another embodiment similar in many respects to those shown and discussed above with reference to FIGS. 3 and 4, with like reference numerals indicate similar structure. In this embodiment, however, the distal end 26 of the first, (e.g., proximal) elongate member 22 does not include a reduced diameter portion and does not extend into the lumen 44, but rather forms a butt joint with the proximal end 48 of the tubular member. Any of the attachment techniques discussed above may be used to form the joint.

Figure 6:
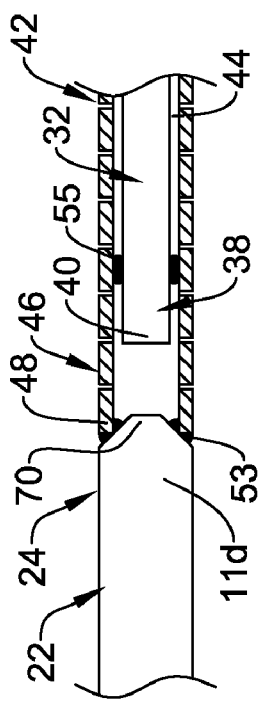
FIG. 6 is a cross-sectional view similar to that of FIG. 3, but showing an alternative construction for the junction between the proximal and distal sections.

Refer now to FIG. 6, which shows another embodiment similar to those shown and discussed above, with like reference numerals indicating similar structure. In this embodiment, however, rather than having an extended reduced diameter portion 68 including a constant diameter portion 71, as in FIGS. 3 and 4, or a butt joint as in FIG. 5, the distal end 30 of the first, (e.g., proximal) elongate member 22 includes a tapering portion 70 that extends only slightly into the lumen 44, and the attachment points/regions 53 is disposed along the tapering portion 70. Again, any of the attachment techniques discussed above may be used.

Figure 7:
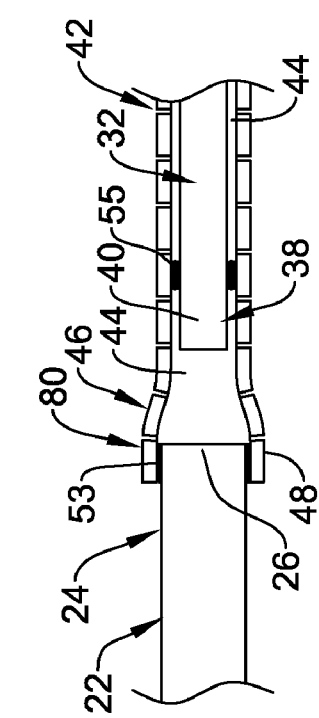
FIG. 7 is a cross-sectional view similar to that of FIG. 3, but showing an alternative construction for the junction between the proximal and distal sections.

Refer not to FIG. 7, which shows another embodiment which in many respects is similar to those shown and discussed above; with like reference numerals indicating similar structure. In this embodiment, however, the distal end 30 of the first, (e.g., proximal) elongate member 22 does not include a reduced diameter portion, but rather the proximal end 48 of the tubular member includes a flared region 80 such that the lumen 44 along the flared region includes an increased inner diameter. As such, the distal end 26 of the first elongate member 22 can extend into expanded lumen 44 defined by the flared region 80, and attachment between the two structures can be made, for example, at attachment points 53. Again, any of the attachment techniques discussed above may be used.

Figure 8:
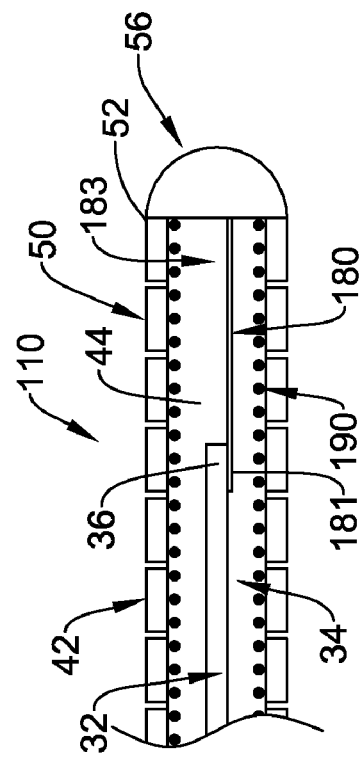
FIG. 8 is a cross-sectional view showing an alternative example embodiment of a distal construction.

Refer now to FIG. 8, which is a cross-sectional view of the distal end of another example embodiment of a device 110, such as a guidewire or the like, which can include similar structure to those discussed above, with like reference numerals indicate similar structure. In this embodiment, however, the device 110 includes some additional/alternative structure in the distal portion thereof. For example, while the device includes a distal tip 56, for example, as discussed above, the distal end 36 of the second (e.g. distal) elongate member 32 does not extend to the distal tip, but rather ends at a point proximal from the distal tip 56. The tubular member 42 does extend to, and is attached to the distal tip 56. This embodiment also includes a structure 180, such as a shaping ribbon or wire, or the like. The structure 180 includes a proximal end 181 attached to the distal end 36 of the second elongate member 32, and extends distally, and has a distal end 183 attached to the distal tip 56. The structure 180 can be made from a variety of materials, including metals, alloys, plastics, or other suitable materials, for example, those discussed above. The cross-section of the structure 180 can be of a variety of shapes, including round, oval, flat, ribbon-shaped, rectangular, square, or any other suitable shape or a combination thereof.

The tip construction can also include an elongate flexible member 190, such as a helical coil or a polymer sheath, disposed within the lumen 44 of the tubular member 42 and disposed about at least a portion of the second elongate member 32 and/or at least a portion of the structure 180. In the embodiment shown, the flexible member 190 is a helical coil. Such a coil 190 may act to reinforce the distal tip of the device, and/or can act as a radiopaque marker, or both. The coil can be formed of or comprise wire or ribbon that has a solid cross-section, and that can include any of a variety of cross-sectional shapes, including round, oval, flat, ribbon-shaped, or any other suitable shape or a combination thereof. The coil 190 can be made of a variety of materials, including metals, alloys, plastics, or other suitable materials, including radiopaque materials, many of which were discussed above. Some examples of other suitable tip constructions and structures that can be used are disclosed in U.S. Pat. No. 6,918,882, and U.S. patent application Ser. No. 10/086,992 filed Feb. 28, 2002 (Pub. No. U.S. 2003/0069521), which are incorporated herein by reference.

It should also be understood that the device 10 or 110, or others, can include additional structure, such as additional shaping or safety wires or ribbons, marker bands and/or coils, additional inner or outer coils, inner or outer sheaths or coatings, and the like. Those of skill in the art and others will recognize how to incorporate such additional structures into the device, as is generally known.

Additionally, in some embodiments, a coating, for example a lubricious (e.g., hydrophilic) or other type of coating may be applied over portions or all of the medical devices or structures discussed above. For example, such a coating may be applied over portions or the entire device 10 or 110, including, for example, device sections 14/16, the first and second elongated members 22/32, the tubular member 42, the distal tip 56, or other portions of the device 10 or 110. Hydrophobic coatings such as fluoropolymers, silicones, and the like provide a dry lubricity which improves guide wire handling and device exchanges. Lubricious coatings improve steerability and improve lesion crossing capability. Suitable lubricious polymers are well known in the art and may include hydrophilic polymers such as, polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portions are coated with a fluoropolymer, such as polytetrafluroethylene (PTFE).

The use of a coating layer in some embodiments can impart a desired flexibility to the shaft 12. Choice of coating materials may vary, depending upon the desired characteristics. For example, coatings with a low durometer or hardness may have very little effect on the overall flexibility of the device 10. Conversely, coatings with a high durometer may make for a stiffer and/or less flexible shaft.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

I claim:

1. An intracorporeal medical device comprising:
    a first elongate member having a proximal region, a distal region and a distal end;
    wherein the proximal region of the first elongate member has a circular cross section defining an outer diameter;
    an elongate tubular member comprising a metallic material and defining a lumen there through, the tubular member having a proximal region, a proximal end, a distal region, and a distal end, the proximal region of the tubular member attached to the distal region of the first elongate member at a first attachment region, the tubular member extending in a distal direction away from the first elongate member from the proximal end of the tubular member to the distal end of the tubular member;
    wherein the elongate tubular member has a circular cross section defining an outer diameter;
    wherein the outer diameter of the elongate tubular member is the same length as the outer diameter of the first elongate member; and
    a second elongate member having a proximal region, a proximal end, a distal region, and a distal end, the second elongate member disposed within the lumen of the tubular member, an outer surface of the proximal region of the second elongate member attached to an inner surface of the proximal region of the elongate metallic tubular member at a second attachment region.

2. The intracorporeal device according to claim 1, wherein the first elongate member and the second elongate member are not directly attached to one another.

3. The intracorporeal device according to claim 1, wherein a distal end of the first elongate member is attached to the tubular member.

4. The intracorporeal device according to claim 1, wherein a proximal end of the tubular member is attached to the first elongate member.

5. The intracorporeal medical device according to claim 1, wherein the tubular member extends distally such that at least a portion of the distal region of the tubular member is disposed adjacent to or distally of the distal region of the second elongate member.

6. The intracorporeal medical device according to claim 1, wherein the distal end of the tubular member is disposed adjacent to or distally of the distal end of the second elongate member.

7. The intracorporeal medical device according to claim 1, wherein the tubular member has a length, and the second elongate member extends within the lumen of the tubular member along at least about 50% of the length thereof.

8. The intracorporeal medical device according to claim 1, further including a distal tip, and wherein the tubular member extends distally to a point adjacent the distal tip and is attached to the distal tip.

9. The intracorporeal medical device according to claim 1, further including a distal tip, and wherein the second elongate member extends distally to a point adjacent the distal tip and is attached to the distal tip.

10. The intracorporeal device according to claim 1, wherein a distal end of the first elongate member extends into the lumen of the tubular member.

11. The intracorporeal device according to claim 1, wherein at least a portion of the distal region of the first elongate member is tapered.

12. The intracorporeal device according to claim 1, wherein at least a portion of the proximal region of the tubular member is tapered.

13. The intracorporeal device according to claim 1, wherein the first elongate member has a solid cross-section and the second elongate member has a solid cross-section.

14. The intracorporeal device according to claim 1, wherein the first elongate member comprises a first metallic material and the second elongate member comprises a second metallic material different from the first metallic material.

15. The intracorporeal device according to claim 1, wherein the second elongate member comprises a nickel titanium alloy.

16. The intracorporeal device according to claim 1, wherein the tubular member comprises a nickel titanium alloy.

17. The intracorporeal device according to claim 1, wherein the tubular member comprises a tubular wall defining a plurality of cuts or slots formed therein.

18. The intracorporeal device according to claim 17, wherein the tubular member extends along a longitudinal axis, and the cuts or slots include a length extending about the longitudinal axis, and the length of the cuts or slots is oriented substantially perpendicular to the longitudinal axis.

19. The intracorporeal device according to claim 17, wherein the cuts or slots are formed in groups of two defined at generally corresponding points along the length of the tubular member, and wherein the two cuts or slots within each group are located on opposite sides of the tubular member.

20. The intracorporeal device according to claim 19, wherein each of the groups of cuts or slots is disposed at a 90 degree rotation around the axis with respect to the adjacent groups.

21. The intracorporeal device according to claim 17, wherein the cuts or slots have a density and wherein the density of cuts or slots per unit length of the tubular member increases in the distal direction along the tubular member.

22. The intracorporeal device according to claim 17, wherein the cuts or slots have a depth and wherein the depth or size of the cuts or slots increases in the distal direction along the tubular member.

23. The intracorporeal device according to claim 1, wherein a proximal end of the second elongate member is spaced from the distal end of the first elongate member.

24. The intracorporeal device according to claim 1, wherein a proximal end of the second elongate member is in contact with a distal end of the first elongate member.

25. The intracorporeal device according to claim 1, wherein the second elongate member includes a taper.

26. A medical guidewire comprising:
an elongated proximal core member including a proximal region and a distal region;
an elongated tubular member comprising a metallic material and defining a lumen there through and having a distal end, a distal region and a proximal region, the proximal region of the tubular member being connected to the distal region of the proximal core member at a first attachment region such that the tubular member extends in a distal direction away from the distal region of first elongate member from the proximal region of the tubular member toward distal region of the tubular member;
wherein the proximal core member has a circular cross section defining an outer diameter;
wherein the elongate tubular member has a circular cross section defining an outer diameter;
wherein the outer diameter of the proximal core member is the same length as the outer diameter of the elongate tubular member;
an elongated distal core member having a distal end, a proximal region and a distal region, the distal core member disposed within and extending along at least a portion of the lumen of the elongated metallic tubular member, and an outer surface of the proximal region of the distal core member connected to an inner surface of the proximal region of the tubular member at a second attachment region; and
wherein the distal end of the elongated tubular member and the distal end of the elongated distal core member are longitudinally aligned.

27. The medical guidewire according to claim 26, wherein the proximal core member and the distal core member are not directly attached to one another.

28. The medical guidewire according to claim 26, further including a distal tip, and wherein the tubular member extends distally to a point adjacent the distal tip and is attached to the distal tip.

29. The medical guidewire according to claim 26, wherein the proximal core member comprises a metallic material, the tubular member comprises a nickel titanium alloy, and the distal core member comprises a nickel-titanium alloy.

30. The medical guidewire according to claim 26, wherein the tubular member comprises a tubular wall defining a plurality of cuts or slots formed therein.

31. The medical guidewire according to claim 26, wherein the distal core member includes a proximal end, and the proximal core member includes a distal end, and the proximal end of the distal core member is spaced from the distal end of the proximal core member.

32. The medical guidewire according to claim 26, wherein a proximal end of the distal core member is in contact with a distal end of the proximal core member.

33. A method of manufacturing an intracorporeal medical device, the method comprising:
providing a first elongate member having a proximal region, a distal region and a distal end;
wherein the proximal region of the first elongate member has a circular cross section defining an outer diameter;
providing an elongate tubular member comprising a metallic material and defining a lumen there through, the tubular member having a proximal region, a proximal end, a distal region, and a distal end;
wherein the elongate tubular member has a circular cross section defining an outer diameter;
wherein the outer diameter of the elongate tubular member is the same length as the outer diameter of the proximal region of the first elongate member;
providing a second elongate member having a proximal region, a proximal end, a distal region, and a distal end;

disposing the second elongate member within the lumen of the tubular member;

attaching an outer surface of the proximal region of the second elongate member to an inner surface of the proximal region of the elongate metallic tubular member; and attaching the proximal region of the tubular member to the distal region of the first elongate member such that the tubular member extends in a distal direction away from the distal region of the first elongate member from the proximal region of the tubular member toward distal region of the tubular member.

34. The method according to claim 33, wherein the proximal region of the second elongate member is attached to the proximal region of the elongate metallic tubular member by welding, soldering, adhesive bonding, or mechanical interlocking.

35. The method according to claim 33, wherein the proximal region of the tubular member is attached to the distal region of the first elongate member by welding, soldering, adhesive bonding, or mechanical interlocking.

36. The method according to claim 33, further comprising providing a distal tip, and attaching the distal tip to the tubular member.

37. The method according to claim 33, further comprising providing a distal tip, and attaching the distal tip to the second elongate member.

38. The method according to claim 33, wherein the intracorporeal medical device comprises a guidewire, the first elongate member comprises a proximal core member, the second elongate member comprises a distal core member, and the elongate tubular member comprising a structure that interconnects the distal region of the proximal core member and the proximal region of the distal core member, and also extends distally about the distal region of the distal core member.

* * * * *